United States Patent [19]
Hirsh

[11] Patent Number: 5,612,783
[45] Date of Patent: Mar. 18, 1997

[54] MODIFIED INTRINSIC STATE SPECTRAL ANALYSIS APPARATUS AND METHOD

[75] Inventor: Allen G. Hirsh, Silver Spring, Md.

[73] Assignee: Organ, Inc., Chicago, Ill.

[21] Appl. No.: 409,064

[22] Filed: Mar. 23, 1995

[51] Int. Cl.$^6$ ..................................... G01J 3/447
[52] U.S. Cl. ........................... 356/327; 356/367
[58] Field of Search ..................... 356/327, 364, 356/365, 366, 367

[56] References Cited

U.S. PATENT DOCUMENTS 5,457,535   10/1995   Schmidtke et al. ............. 356/364

OTHER PUBLICATIONS

Instrumentation for Automated Determination of Protein Stability, Wesley E. Sites, Michael P. Byrne, Jack Aviv, Murray Kaplan, and Paul M. Curtis, Analytical Biochemistry 227, 112–122; 1995.

*Primary Examiner*—F. L. Evans
*Attorney, Agent, or Firm*—Oliff & Berridge

[57] ABSTRACT

An apparatus and method for modified intrinsic state spectral analysis determines a proportion of a plurality of intrinsic structures of an optically active molecule. A spectropolarimeter generates a plurality of intrinsic spectra. Each of the plurality of intrinsic spectra is an intrinsic state vector corresponding to a plurality of intrinsic molecular structures. The spectropolarimeter also generates a spectrum for a sample of the optically active molecule. The sample spectrum is a sample state vector of the optically active molecule. A controller determines a plurality of estimate state vectors based on a plurality of perturbed intrinsic state vectors. Each of the plurality of perturbed intrinsic state vectors corresponds to a perturbed intrinsic structure. An optimum proportion of the plurality of perturbed intrinsic state vectors corresponds to each estimate state vector. The plurality estimate state vectors are matched against the sample state vector to determine a best match estimate state vector. The optimum proportion of the best matched estimate state vector is the proportion of the perturbed intrinsic molecular structures in the sample of the optically active molecule.

15 Claims, 8 Drawing Sheets

MODIFIED INTRINSIC STATE SPECTRAL ANALYSIS APPARATUS AND METHOD

BACKGROUND

The invention relates to analysis of molecular structures using spectropolarimeters. In particular, an apparatus and method are provided to determine the proportional combination of structures of optically active substances in solution.

The technique of spectropolarimetry or circular dichroic analysis (CD) is the preferred technique for determining the structures of optically active molecules in solution. Many alternative techniques exist, including nuclear magnetic resonance, hydrogen exchange, calorimetry, fluorescence polarization, fluorescence lifetime, steady state fluorescence measurement, differential light absorption measurements and standard spectrophotometry all of which yield information about the structure of molecules including those that are not optically active. However, CD is preferred because it is sensitive to basic structural forms and defines the percentages of these forms globally in the molecule over a wide range of conditions. The alternative techniques are either insensitive to structure directly or measure structure much more locally than CD.

The general method for utilizing CD data to obtain structure in test solutions of molecules is to develop a set of basis vectors. A set of basis vectors is a set of spectra which characterizes the authentic differential absorption of the left and right circularly polarized light in samples that are putatively of one pure form only. For example, spectra can be vectors generated to represent protein molecules that are entirely in the alpha helical, beta sheet or other pure forms. Based on the type of spectra (basis vectors) created for the pure forms, protein or other molecules are characterized by these pure forms.

Particular molecules in a solution can be modeled on the basis of a set of appropriately chosen pure forms. For example, a block copolymer crystal is observed to be substantially in one of several fundamental forms. If it can be shown that the copolymer in solution is also this fundamental form then it can provide an experimentally estimated vector for a molecule that is purely of the fundamental form.

Generally, a set of basis vectors representing all of the forms that are present in significant quantities in a sample of a molecule is generated. Typically, for proteins, this includes a minimum of four or five forms. In some situations eight or nine vectors may be necessary to distinguish certain closely related forms.

Conventionally, a sample spectrum of the sample molecule is generated and stored in a memory as a sample vector. Standard mathematical techniques are used to produce a linear combination of the basis vectors which will be used to characterize this sample molecular structure. Alternatively, a basis set can be used which is a set of vectors each of which is from samples thought to have well characterized structures. These are then substitute basis vectors. An estimate of the percentage of each of the basis forms contained in the sample molecular structure is then generated based on mathematical combinations of the substitute basis vectors that are optimized to fit the sample vector. The estimate is a model of the sample molecule structure. Knowledge of the structure of each of these substitute basis vectors together with this model allows a further estimate of the predominant structure of the sample molecule in terms of a true basis set.

The fundamental problem with the above mentioned approach is the conventional assumption that the sample molecule is predominantly in one structural form. In general this is incorrect because the sample molecule exists in more than one structural form in a solution. For example, proteins at body temperature are very close to 100% in a native state. Unfortunately, under industrial conditions, high temperatures, low temperatures, high pH's, low pH's, very low salt, very high salt, or the presence of surface modifying organic materials such as detergents, a significant percentage of the molecules are destabilized into one or more alternative forms. Accordingly, assuming the existence of one structural form when several structural forms exist leads to meaningless results.

In addition, current techniques generate the fundamental vectors under different conditions than the conditions under which the sample vectors are generated. Thus, even if current techniques are modified to account for a mixture of sample molecular structures, the fundamental vectors cannot be used to estimate the sample molecular structures. Further, estimated sample vectors using current techniques do not fit actual sample vectors very well.

SUMMARY OF THE INVENTION

This invention thus provides a device and method for analyzing the molecular structures of an optically active substance that avoids the problems discussed above. Specifically, the device and method determine the proportions of a plurality of intrinsic (reference) forms of the test molecule including determination of the extent of structural change of any desired subset of the intrinsic forms.

In order to achieve the above and other objects, a method for determining a proportion of a plurality of intrinsic structures of an optically active substance in a sample of the optically active substance is provided that includes generating a plurality of intrinsic spectra. Each intrinsic spectrum corresponds to one of a plurality of intrinsic molecular structures. The pure native state or the pure heat-unfolded state of a protein are examples of intrinsic structures. A sample spectrum of the optically active substance is also generated.

A plurality of estimated spectra is generated. Each estimated spectra corresponds to a proportional combination of at least two perturbed intrinsic spectra of the optically active substance.

A best match estimated spectrum is selected from the plurality of estimated spectra. The best match estimated spectrum is the estimated spectrum that most closely matches the sample spectrum of the optically active substance. The proportional combination of the best match estimated spectrum is outputted as the proportional combination of the plurality of perturbed intrinsic structures of the sample of the optically active substance.

A device is provided for determining the proportional combination of the plurality of intrinsic structures of the sample of the optically active substance. The device includes a spectrum generating device, an I/O device inputting spectrum data generated by the spectrum generating device and a memory device coupled to the I/O device.

An estimated spectra determining means determines a plurality of estimated spectra based on the plurality of intrinsic spectra. A best match selection means selects one of the plurality of estimated spectra as a best match estimated spectra of the optically active substance.

A controller controls the I/O device, the memory device, the estimate state vector determining means and the best match selection means to generate the proportional combination of the plurality of intrinsic structures of the sample of the optically actives substance.

BRIEF DESCRIPTION OF THE DRAWINGS

The invention will be described in detail with reference to the following drawings, wherein.

DETAILED DESCRIPTION OF PREFERRED EMBODIMENTS

Figure 1:
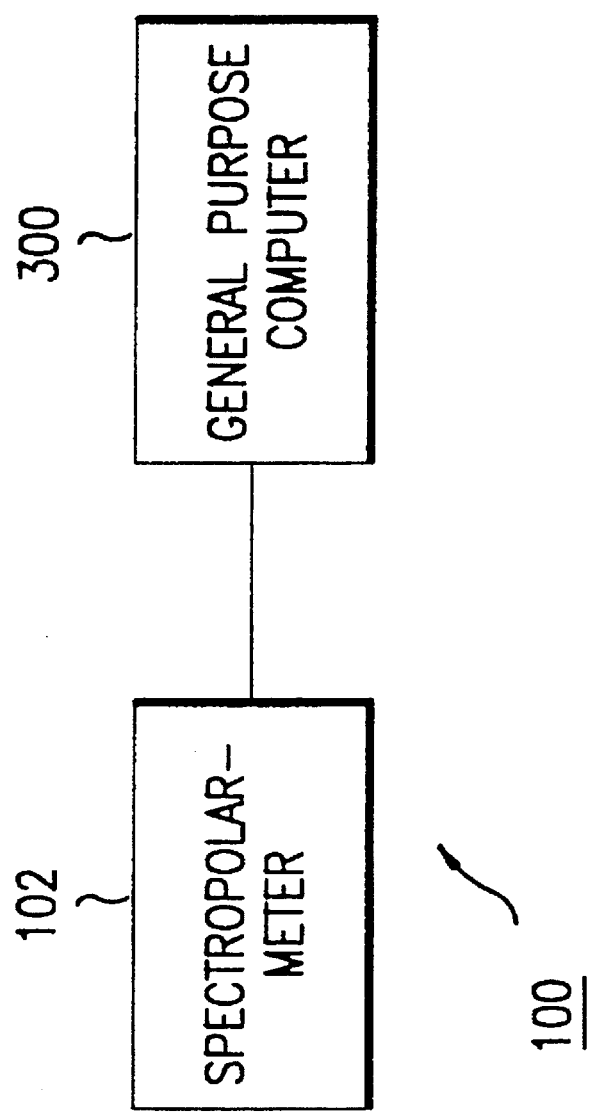
FIG. 1 is a block diagram of the modified intrinsic state spectral analysis system.

FIG. 1 a modified intrinsic state spectral analysis system 100. The system includes a spectropolarimeter 102 and a general purpose computer 300.

The spectropolarimeter 102 generates a beam of circularly polarized light. Circularly polarized light comprises a vertical component and a horizontal component forming a wave vector. The beam may be right circularly polarized or left circularly polarized. The beam of circularly polarized light generated by the spectropolarimeter 102 oscillates very rapidly between the right and left circular polarization. The spectropolarimeter beam is split into two parts. A first part passes through a sample of molecules and then to a detector while a second part passes directly to the detector. The adjusted difference between the intensities is the amount absorbed by the sample molecules. A function of this difference, called ellipticity, is the output data generated by the spectropolarimeter 102.

Figure 2:
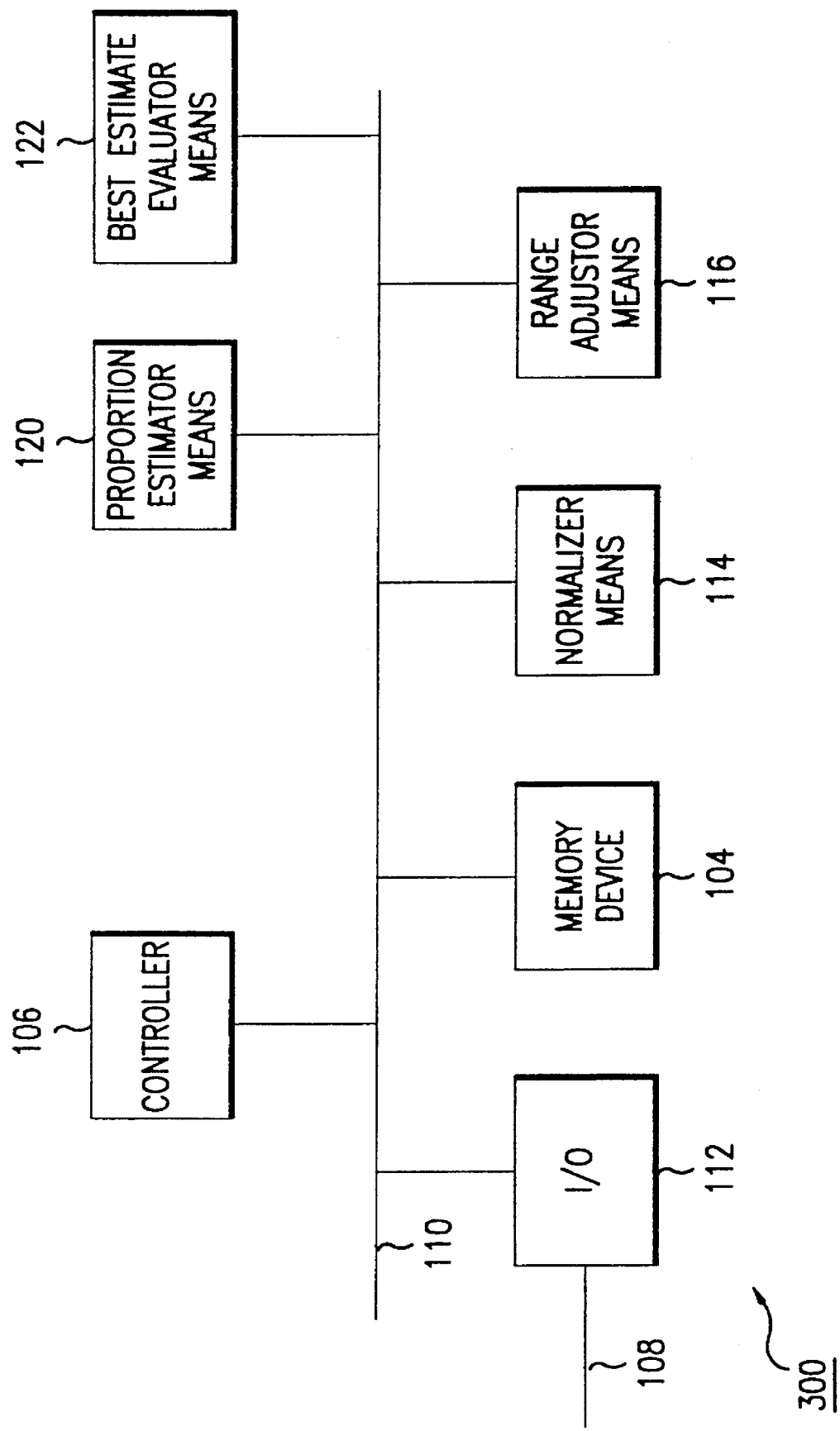
FIG. 2 is a block diagram of the modified intrinsic state spectral analysis device.

FIG. 2 shows a block diagram of the general purpose computer 300 including an I/O unit 112, a controller 106 and a memory device 104. The I/O unit 112 receives output data generated by the spectropolarimeter 102 and stores the output data into the memory device 104.

Figure 3:
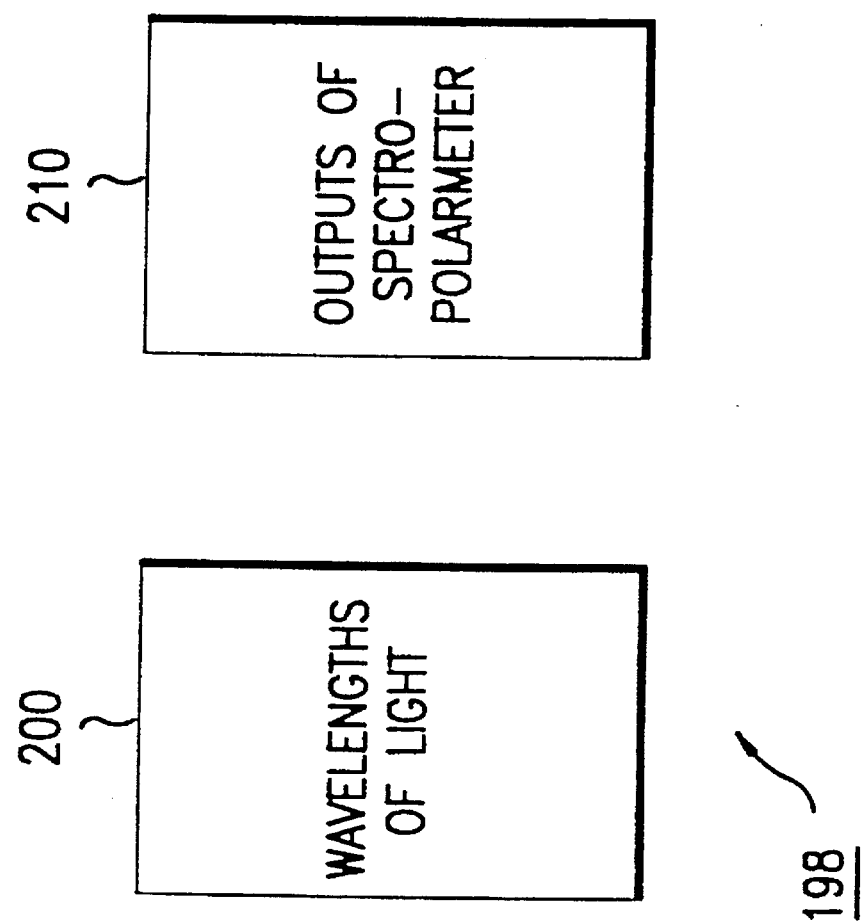
FIG. 3 is a diagram of a file containing an intrinsic spectra.

FIG. 3 shows a file structure 198 in the memory device 104 of the output data generated by the spectropolarimeter 102. The file structure 198 has two corresponding columns of data 200 and 210. Column 200 contains all the wavelengths of light emitted by the spectropolarimeter 102 and column 210 contains the output data generated by the spectropolarimeter 102 corresponding to each wavelength in column 102.

A molecule which is optically active absorbs a different amount of right circularly polarized light than left circularly polarized light. Thus, because the spectropolarimeter beam is rapidly oscillated between the right and left circularly polarized light, the amount of light absorbed by the sample also oscillates rapidly. The spectropolarimeter 102 calculates the time average difference values of the absorbed amount of right and left circularly polarized light and stores a function of these difference values in column 210 of the file 198 shown in FIG. 3.

The wavelength is systematically varied in time between two prefixed limits. The wavelength is changed at a rate much slower than the sampling rate to generate the differential sample molecule light absorption spectrum over a wide wavelength range. This set of difference values is called the raw ellipticity of the sample of molecules. Thus, the raw ellipticity of the sample of molecules comprises the difference values corresponding to all the wavelengths that are in column 200.

The output data that is generated for each wavelength varies depending on the molecular structure of the sample. Thus a particular molecular structure may absorb a greater amount of a horizontal component of the circularly polarized light resulting in a shift of the wave vector of the light. Because of the differential absorbance of the left and right circularly polarized light by the sample molecules, an elliptically varying light vector is generated as opposed to the initial linearly varying vector. The arctangent of the ratio of a major/minor axis of the ellipse is the ellipticity which is stored in column 210 of the file 198.

The differential absorbance is calculated by the spectropolarimeter 102 and for each wavelength, the spectropolarimeter 102 outputs a time average signal which is a function of the net difference in absorbance of the sample. This function of the net difference in absorbance is the ellipticity and is a measure of the deviation from circularity of the light wave vector after it passed through the sample. Accordingly, the values contained in column 210 of the file 198 is referred to as the ellipticity data.

The wavelengths are generally in nanometers (nm) varying from about 170 nm to infrared wavelengths of greater than 1000 nm. For most commonly used applications, the light is in the ultraviolet region having wavelengths between 170 nm and 300 nm.

In general, either the spectropolarimeter 102 or the controller 106 normalizes the ellipticity data. This normalization converts the measured ellipticity into ellipticity per molecular solution subunit per unit path length so that molecules of a similar structure, but different sizes, concentrations and volumes can be compared. This ability to compare the ellipticity of similarly structured molecules of different sizes is very important. The unnormalized ellipticity data output from the spectropolarimeter 102 is multiplied by 100 and then divided by the concentration of measured molecular subunits in moles per liter and then divided by the path length in centimeters. Thus, the actual ellipticity unit in the column 210 is in thousands of milli-degrees times $cm^2$ divided by moles.

Figure 4:
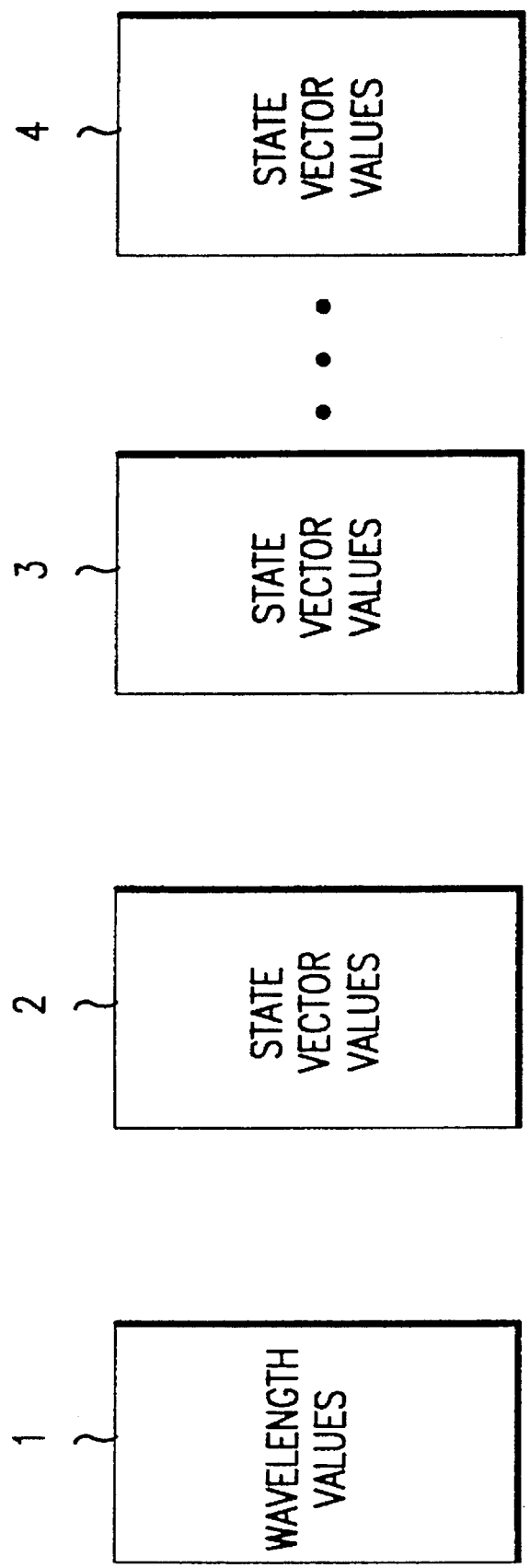
FIG. 4 is a diagram of a file containing pure molecular form (basis) spectra.

FIG. 4 shows a structure of a file 298 containing perturbation vectors. Perturbation vectors are records of ellipticity versus wavelength for pure molecular forms. In protein science, an example of a typical pure molecular form is an alpha helix. The alpha helix is a structure of protein molecules in which the backbone of the molecule is coiled in an alpha helical structure and substantially linear over moderate spans. A second pure molecular form is a beta sheet. A beta sheet is a structure of a protein molecule in which residues (side chains of amino acids for example) are pointing outward and the backbone is arranged in a planer fashion of one backbone unit to another backbone unit to create what amounts to a pleated sheet. A third pure molecular form is a random coil in which backbone elements are randomly oriented in space. Of course, it is appreciated that there are many other pure molecular forms of which the alpha helix, the beta sheet and the random coil are examples from the analysis of proteins in aqueous solution.

The file 298 of FIG. 4 has columns 1, 2, 3, ... M where M is an integer. Column 1 of file 298 contains wavelength values corresponding to the wavelength values contained in the column 200 of the file 198. Each of columns 2-M of the file 298 contain state vector values corresponding to one of the pure molecular forms such as alpha helix, beta sheet and random coil. The state vector values for pure molecular forms can be obtained through generally available literature or generated by the spectropolarimeter 102 using samples of each pure molecular form.

Figure 5:
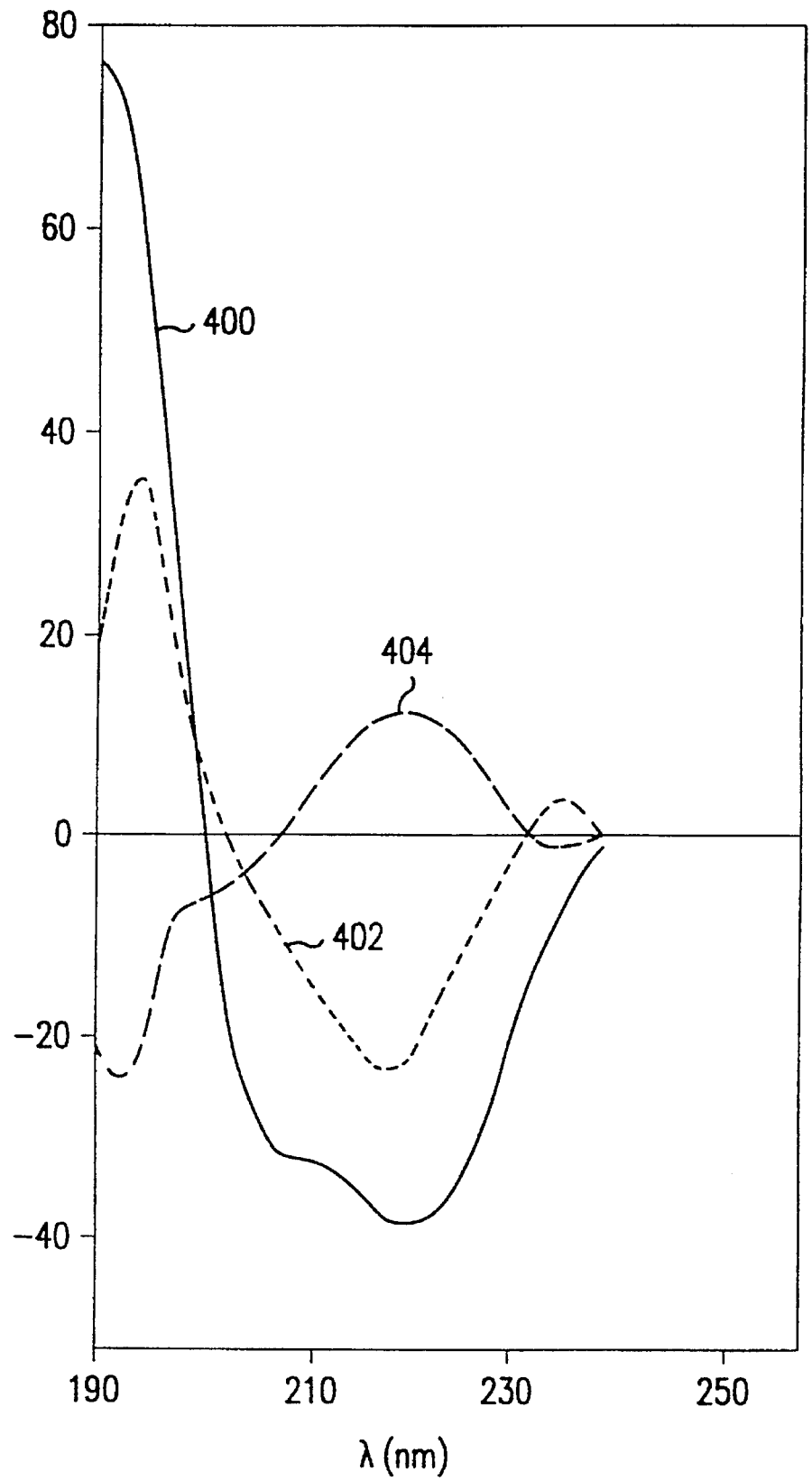
FIG. 5 shows spectra graphs for three pure molecular forms.

The structures of these pure molecular forms are represented by the ellipticities at different wavelengths shown by curves 400, 402 and 404 in FIG. 5. The X axis is the wavelength and the Y axis is the ellipticity value corresponding to three pure molecular forms. Each curve represents one pure molecular form. Curve 400 may represent a plot of the values in column 2 along the Y axis versus the wavelength values in column 1 along the X axis. Curves 402 and 404 correspond to values in column 3 and 4, respectively. As long as the ellipticity values are taken over a fairly broad wavelength range (preferably at least 195 nm to 240 nm for proteins), the differences between the curves are significant and the likelihood that a curve for a particular sample is produced by more than one distinct composite of these fundamental underlying curves (called degeneracy) is fairly small.

Large molecular structures such as protein molecules naturally assume particular states called intrinsic states. Each of these intrinsic states is a unique structure of the same protein and is characterized by a state vector called the intrinsic state vectors. For example, a protein in a native state has a very tight structure while the same protein molecule unfolded has a different, looser structure. At most concentrations of the molecules of interest, the intrinsic state vector for one intrinsic state is substantially independent of the intrinsic state vector for another intrinsic state. Thus, for a sample containing a protein mixture of several intrinsic states, the state vector for the sample is the linear combination of the individual intrinsic vectors.

Further, each intrinsic state comprises a plurality of perturbation states. An intrinsic state of a molecule corresponds to a specific intrinsic structure of the molecule. In general, these structures comprise substructures an example of which are the structures of the pure molecular forms such as alpha helices and beta sheets in proteins. An intrinsic structure comprises a mixture of the pure molecular forms. The proportion of each intrinsic structure in the mixture can change without changing the intrinsic structure itself. Accordingly, changing the proportions of the pure molecular forms of one or more of the intrinsic structures is perturbing the intrinsic state of the molecule. Each unique mixture corresponds to a proportion of the intrinsic states of the molecule each intrinsic state of which may be perturbed.

To determine the molecular structures of a sample, a set of files 198 is created. Each file 198 contains the intrinsic state vectors of the intrinsic states of the sample molecule as measured by the spectropolarimeter 102. In addition, a file 298 is created that contains the state vectors of a plurality of pure molecular forms that may be present in the sample molecule. The method provided by this invention determines the molecular structures of the sample molecule in terms of the percentages of the intrinsic states of the molecule and the perturbation state of each intrinsic state.

As an example of this determination, the unfolded state of a protein, produced by destroying the native state structure through very high or low temperatures, is in a loose high entropy form and this unfolded protein structures itself in various ways as the temperature or other independent variable such as pH, changes. To determine the change of structure of the unfolded protein, the state vectors in columns 2-M in the file 298 are used to systematically vary the state vector in column 210 of the file 198 of one or more of the intrinsic state vector files 198. This process continues until the modified state vector set best matches the actual state vector of the sample generated by the spectropolarimeter 102. For example, the state vector of the intrinsic state in column 210 of the file 198 can be perturbed by subtracting 5% of column 2 (alpha helix), subtracting 5% of column 3 (beta sheet) and then adding 10% of column 4 (random coil). The resulting modified state vector is compared to the actual state vector of the sample molecules generated by the spectropolarimeter. This process hypothesizes that 5% of the alpha helical structure of the structure of the intrinsic state represented by the intrinsic vector in column 210 of the file 198, measured at high temperature, is converted to the random coil structure, and 5% measured of the beta sheet structure of the intrinsic structure is converted to the random coil structure. If this modified intrinsic state better matches the state vector of the sample molecules than previous perturbations, then the process determines a structure transformation of the intrinsic structure from one perturbed state into another, more preferred, perturbed state.

Since no part of the protein is removed or destroyed by structure transformations in the actual test solution, and the difference among the perturbed molecular forms are structural only, subtracting a percentage of one pure molecular form must be accompanied by the addition of that amount of one or more other pure molecular form(s). This is conservation of mass. Accordingly, subtracting 5% of alpha helix and 5% of beta sheet must be accompanied by the adding of 10% of some other forms such as random coil, beta-turn, etc. The sum of all changes must therefore be zero.

Adding and subtracting percentages of the pure molecular forms by adding and subtracting the corresponding state vectors in columns 2-M of file 298 while always maintaining a total change of zero, the process predicts which of the pure molecular structures are disappearing and which pure molecular structures are appearing in any of the intrinsic forms being modified as the sample environmental conditions are changed.

Figure 6:
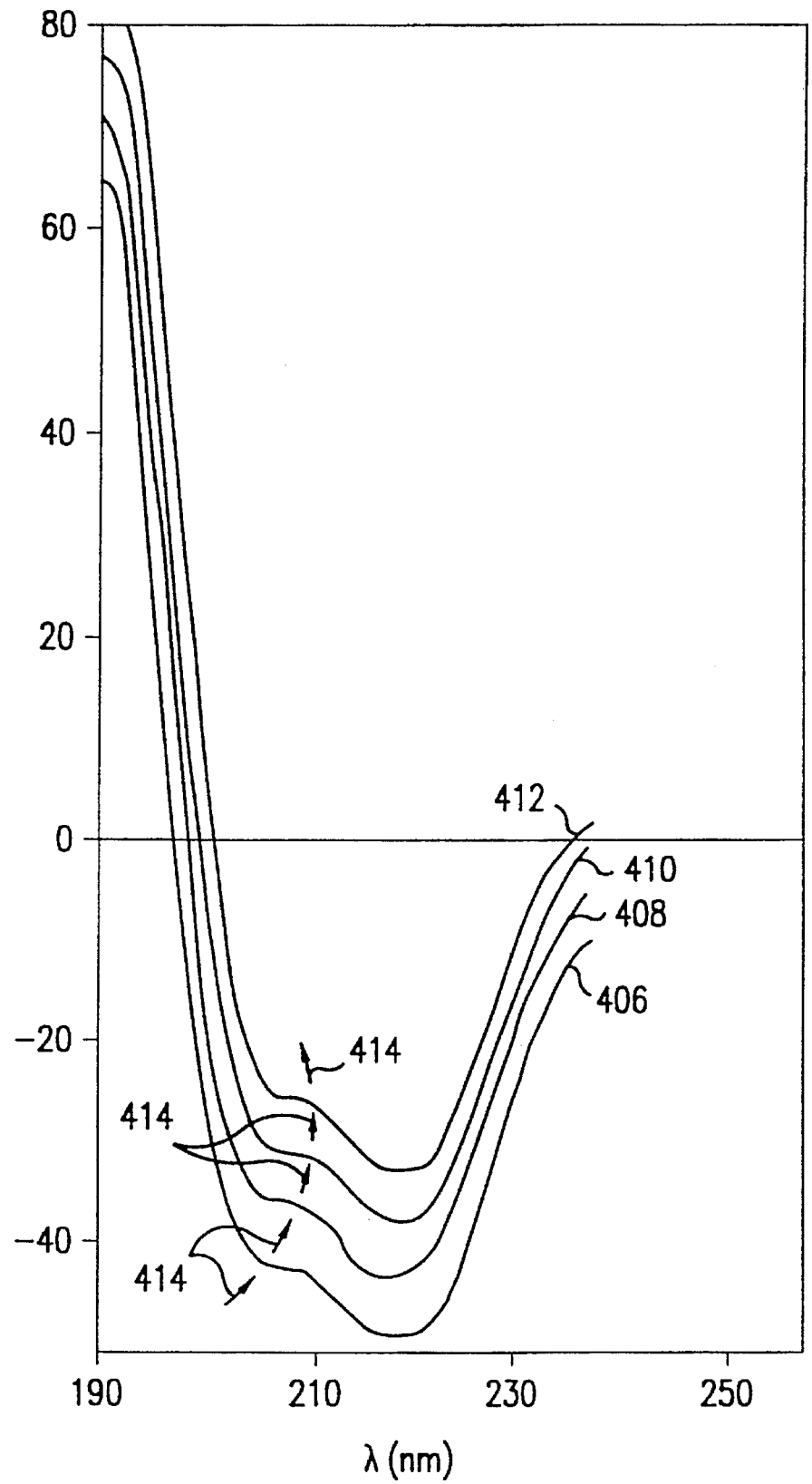
FIG. 6 shows a family of graphs corresponding to one pure molecular form of varying lengths.

FIG. 6 shows a family of curves similar to the curve 400 in FIG. 5. Curves 406, 408, 410 and 412 show how the vector for a particular basic molecular form, such as the alpha helix, varies with the length of the alpha helix. The arrows 414 indicate the direction of curve movement with increasing length. An analogous result occurs with increasing packing density of one alpha helix to other alpha helixes, such as in the folded form of proteins.

When a molecule is measured in the basic molecular form such as the alpha helix of a certain length and packing density, a particular state vector is obtained having values corresponding to each wavelength. If only the length of the alpha helix is changed each of the values of the state vector varies over a certain range. This variation is included in the state vectors of the alpha helix for each specific length as a state vector of a basic molecular form. Thus, the pure molecular forms represented by the state vectors in columns 2-M of the file 298 can include molecular forms that are a function of the packing density, chain length and any other characterizable variations as a function of external conditions. Accordingly, the method of this invention provides a much more sophisticated development of structural change than is presently available.

The intrinsic state vectors represent the actual ellipticity measured under special conditions by the spectropolarimeter 102 for the sample molecules. In general, the intrinsic state vectors are those measurements taken in a situation in which the molecules are, as close as possible, purely in one molecular form. The form's detailed structure is not in general known, that is, the exact proportions of the pure molecular forms comprising this intrinsic form is not known, but it can be expected to be a nearly homogeneous form and the mixtures of these homogeneous forms generates the initial unperturbed intrinsic state vectors when the molecules are under other conditions. To reiterate, the intrinsic state vectors are representative of the ellipticity values when the molecules are entirely of one molecular form.

The pure molecular forms can be subtracted or added within the constraints of conserving the overall number of structures in the molecule to produce a plurality of the intrinsic vectors. This is the perturbation step. The change in the structure of the intrinsic structures can be determined by how well a hypothetical spectrum corresponding to a hypothetical state vector fits the sample spectrum. As perturbations are made to each of the plurality of intrinsic states a state vector is created which can be mixed systematically with the other intrinsic state vectors to produce a best match of the actual sample state vector.

The general purpose computer 300 also includes means for processing the spectropolarimeter output data including normalizer means 114, range adjustor means 116, proportion estimator means 120 and a best estimate evaluator means 122. The above means can be special purpose electronic devices implemented for each means and integrated into one unit, such as an ASIC or a special purpose computer, separate hardware units communicating over the common signal line 110 or a software program executed by the general purpose computer 300. The controller 106 controls the operation of all the above means for analyzing the spectropolarimeter output data to determine structures of a sample of a molecule.

The spectropolarimeter output data are state vectors of the sample molecule comprising differential absorption values across a range of light wavelengths. The normalizer means 114 normalizes the sample molecule state vector based on state vector values of the sample molecule in intrinsic states. The intrinsic state vectors are previously generated by the spectropolarimeter 102, stored in the memory device 104 and provided to the normalizer means 114 by the controller 106 for the normalization process.

The normalization process is necessary when more than one intrinsic molecular structure of the sample molecule are present in significant quantities. Normalization allows treatment of each intrinsic structure to be treated separately from the other intrinsic structures.

Multiple intrinsic structures for samples are often encountered, for example, when a molecule is in a highly degraded form, such as the unfolded state of proteins at high temperatures. Heating many folded proteins to temperatures above their complete unfolding points breaks bonds and oxidizes certain subunits of the proteins. After heating at such high temperatures, the proteins are unable to refold when recooled, indicating permanently changed structures. Therefore, an intrinsic state vector for unfolded proteins is better determined at a temperature such as at the melting point of a protein which may be 30° or 40° C. below the complete unfolding temperature. However, at these temperatures, the proteins often exist in a mixture of two forms, the native compact state and a heat unfolded state. Renormalization allows extraction of each homogeneous form spectrum from a spectrum of a mixture of forms of known proportions.

After the sample state vector is normalized, the range adjustor means 116 determines the initial perturbation range values. The proportion estimator means 120 inputs the range values for the perturbation process.

The sample molecule is assumed to have a plurality of intrinsic state vectors corresponding to a plurality of intrinsic molecular structures. It is also assumed that the sample molecular structure comprises a plurality of pure molecular forms as substructures. Each intrinsic state of the sample molecule can be perturbed by changing a proportion of the pure molecular forms.

The proportion estimator means 120 generates an estimated state vector for different proportions of the pure molecular forms starting from the range of proportions set by the range adjuster means 116. The ranges are determined based on known information about the sample molecule to direct the analysis process in the most promising direction for arriving at a best estimate of the sample molecular structures.

Each intrinsic state vector is perturbed by continuously optimized combination of basic molecular forms within the range set by the range adjuster means 116. This perturbation process generates a plurality of sets of perturbed intrinsic state vectors. Each set of perturbed intrinsic state vectors has a different combination of perturbed intrinsic state vectors than every other set. An estimated state vector of the sample vector is generated based on each set of perturbed intrinsic state vectors. The estimated state vector is an estimate of the structures contained in the sample of molecules.

Each estimated state vector comprises a percentage of each perturbed intrinsic state vector of the set of perturbed intrinsic state vectors. The sum of all the percentages must be 100 percent.

The proportion estimator means 120 determines the best fit proportional combination of the perturbed intrinsic states of the sample molecule based on a sum of squares result for each proportional combination. The sum of squares determined for each proportional combination is a closeness measure of the estimated state vector to the sample vector.

The perturbation estimator means 120 generates the estimated state vector by multiplying each of the perturbed intrinsic state vector by the percentages corresponding to the proportions of that intrinsic vector.

The perturbation estimator means 120 determines a set of derivatives of the sum of squares values for consecutive sets of percentages of the perturbed intrinsic vectors. The sign of these derivatives indicates a direction for the selection of a next set of percentages for the estimated state vector to be generated that will be closer to the sample vector than the estimated state vector determined previously. Following this direction, when a change in the sign of these derivatives occurs, an estimated state vector that is closer to the sample vector is generated. Thus, the proportion estimator means 120 iterates the set of percentages in small fractional increments for the estimated state vector guided by the sum of squares measure. The output of the intrinsic state vector proportion estimator means 120 is the set of percentages that corresponds to the proportional combination of the perturbed intrinsic state vectors that is the closest fit to the sample vector for each estimated state vector.

The estimated state vector generated by the proportion estimator means 120 is input to the best estimate evaluator means 122. The best estimate evaluator means 122 determines a new best estimate of the sample molecule structures. The quality of each estimate is determined by matching the estimated state vector to the sample vector generated by the spectropolarimeter 102 by using the sum of squares technique.

The sum of squares value of the difference between each estimated state vector generated by the proportion estimator means 120 and the sample vector continuously diminishes throughout the process. The final best estimate is determined when the ratio of the sum of squares of a previous estimated state vector minus the sum of squares of a current estimated state vector divided by the sum of squares of the previous estimated state vector is less than a preset minimum value.

Figure 7A:
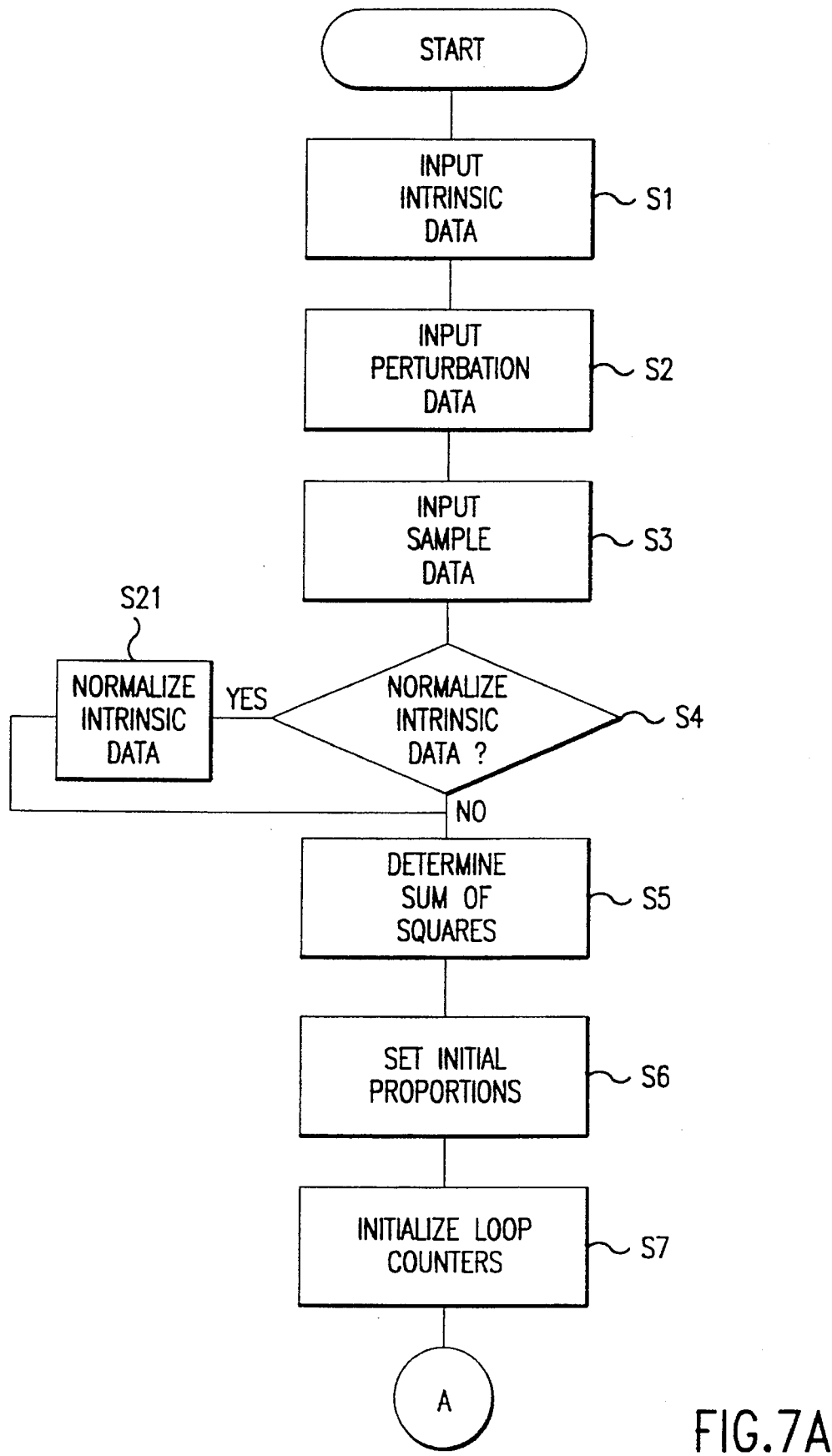
FIGS. 7A and 7B are flow charts of the modified intrinsic state spectral analysis process.
Figure 7B:
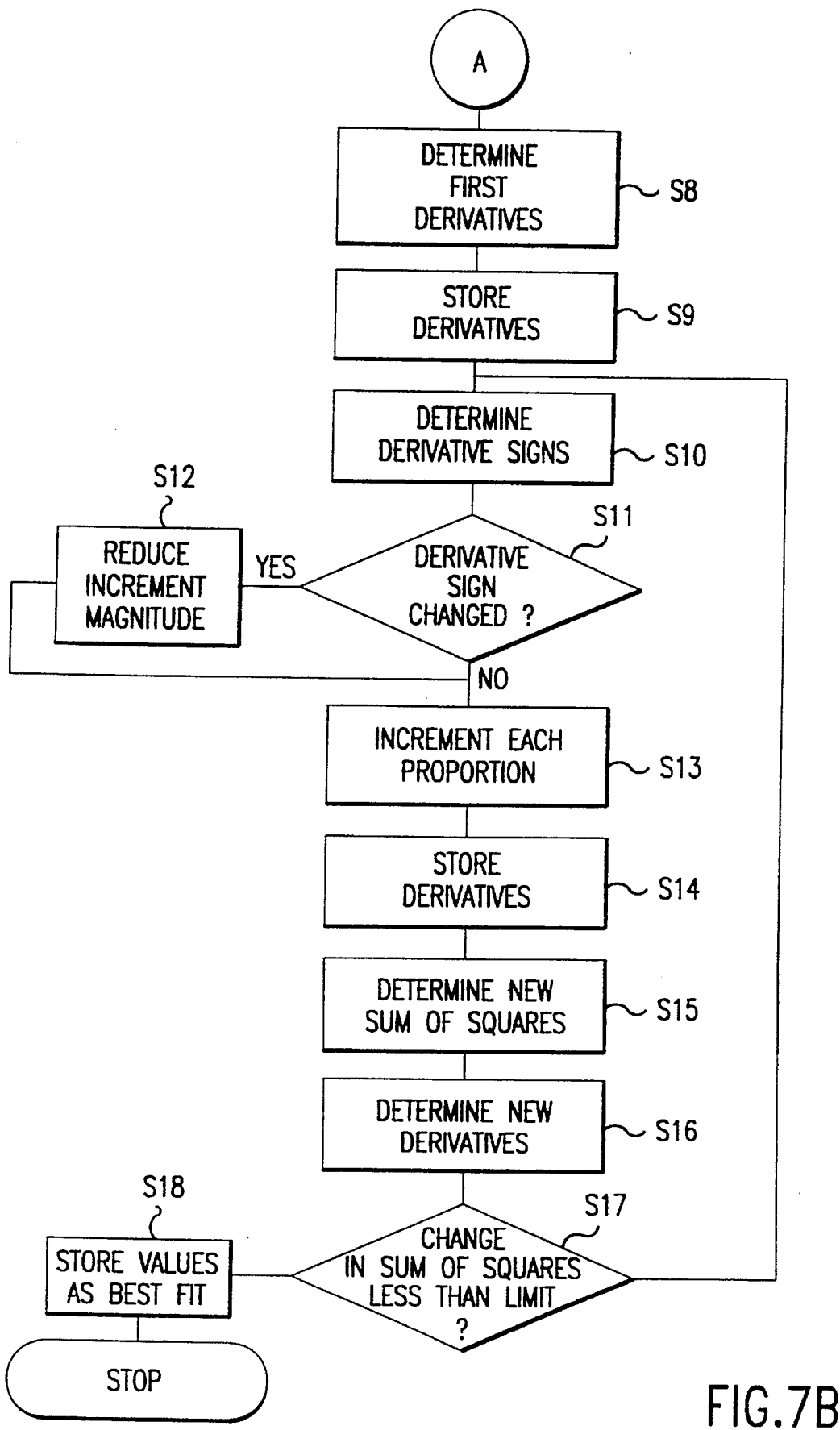

FIGS. 7A and 7B shows a flow chart of the controller 106 process for the method of this invention. In FIG. 7A, after starting, the controller goes to step S1 and inputs the intrinsic state vector data which are the files 198 corresponding to the plurality of intrinsic states. In step S2, the controller 106 inputs the perturbation data which is the file 298 containing the state vector data for all the basic molecular forms associated with the molecules in the test sample. In step S3, the controller 106 inputs the state vector data for the sample of optically active molecule. After inputting the above data, the controller 106 continues to step S4.

In step S4, the controller 106 checks whether the intrinsic state vectors need to be normalized. If the intrinsic vectors need normalization, then the controller 106 jumps to step S21, otherwise, the controller 106 continues to step S5. In step S21, the controller 106 normalizes the intrinsic state vector data and jumps to step S5.

In step S5, the controller 106 determines the mean and sum of squares of the sample vector. Then the controller 106 continues to step S6.

In step S6, the controller 106 sets the range of perturbations determining which of the intrinsic vectors to perturb. The controller 106 determines the best proportion of the unperturbed (all perturbation vectors set to zero) intrinsic state vectors by an inversion of a matrix of a standard set of well known normal equations or other standard mathemtrical techniques for solving these equations such as singular value decompostion. Setting all perturbation vectors to zero almost always leads subsequently to the best fit with high reliability. Then the controller 106 continues to step S7.

An example of equations for the sum of squares ($r^2$) is as follows:

$$r^2 = \sum_{i=1}^{m} \left[ W_i - a_1 v_{1i} - a_2 v_{2i} - \ldots a_{n-1} v_{(n-1)i} - \left(1 - \sum_{j=1}^{j=n-1} a_j\right) * \left(v_n - \sum_{l=2}^{k} b_l u_{1i} + \sum_{l=2}^{k} b_l u_{li}\right) \right]^2 \quad (1)$$

with perturbation of vector number n, $$r^2 = \sum_{i=1}^{m} \left[ W_i - a_1 v_{1i} - a_2 v_{2i} - \ldots a_{n-1} v_{(n-1)i} - \left(1 - \sum_{j=1}^{j=n-1} a_j\right) \right]^2 \quad (2)$$

with zero perturbation. The normal equations set in matrix form are as follows:

$$\tilde{M} = \sum_{i=1}^{m} \begin{bmatrix} -(v_{1i}-v_{ni})*(v_{1i}-v_{ni}) & -(v_{2i}-v_{ni})*(v_{1i}-v_{ni}) & \ldots & -(v_{(n-1)i}-v_{ni})*(v_{1i}-v_{ni}) & -v_{ni}*(v_{1i}-v_{ni}) \\ \cdot & \cdot & & \cdot & \cdot \\ \cdot & \cdot & & \cdot & \cdot \\ \cdot & \cdot & & \cdot & \cdot \\ -(v_{1i}-v_{ni})*(v_{(n-1)i}-v_{ni}) & -(v_{2i}-v_{ni})*(v_{(n-1)i}-v_{ni}) & \ldots & -(v_{(n-1)i}-v_{ni})*(v_{(n-1)i}-v_{ni}) & -v_{ni}*(v_{(n-1)i}-v_{ni}) \end{bmatrix} \quad (3)$$

$$\tilde{D} = \sum_{i=1}^{m} \begin{bmatrix} -W_i*(v_{1i}-v_{ni}) \\ \cdot \\ \cdot \\ \cdot \\ -W_i*(v_{(n-1)i}-v_{ni}) \end{bmatrix} \quad (4)$$

$$\tilde{C} = \begin{bmatrix} a_1 \\ \cdot \\ \cdot \\ \cdot \\ a_{n-1} \end{bmatrix} \quad (5)$$

$$\tilde{C} = \tilde{M}^{-1} * \tilde{D} \quad (6)$$

These normal equations (3)–(6) are the standard set used for determining the minimum sum of squares in a statistical estimation procedure. The sum of squares of the differences between each data point and the mathematical expression defining the estimate (estimator expression) for that data point is generated. Equation (1) sets forth the relationship among a system of N intrinsic states and K basic (perturbation) state of the intrinsic state n (the nth intrinsic state). The partial derivatives of the sum are taken with respect to each independent coefficient of the estimator expression and all of these equations are set equal to zero. If the system is linear, as is the case for step S7 with the unperturbed intrinsic state vectors set to zero, then the relevant sum of squares equation reduces to equation (2), and the coefficients of the normal equations can be solved for by standard matrix inversion. The matrix equation to be solved is equation (6) with each matrix, $\tilde{M}$, $\tilde{D}$ and $\tilde{C}$, defined by equations (3)–(5). In these equations, each ellipticity measurement at wavelength $\lambda_i$ for the first through nth intrinsic state is $V_{1i}$ to $V_{ni}$. Each sample ellipticity at wavelength $\lambda_i$ is $W_i$, and the proportions of each intrinsic state to be found are $a_1$ to $a_{n-1}$ ($a_n$ is determined by $\Sigma a_j = 1$). If perturbations are included as in equation (1) then an additional k perturbation vectors, $\mu_1$ to $\mu_k$ having individual ellipticities at $\lambda_i$ of $\mu_{1i}$ to $\mu_{ki}$ are multiplied by respective perturbation proportions $b_2$ to $b_k$ which become additional unknowns to be solved. In this case, an iterative numerical approximation method must be used, such as in steps S10 to S17.

In step S7, the controller 106 determines the initial best fit estimated state vectors by setting all perturbation vectors to zero and solving the normal equations with only the proportions of the initial intrinsic state vectors as variables.

The matrix of normal equations is inverted, or any other decomposition method for solving for the coefficients of the normal equations is used, and the coefficients which represent the best mixture of unmodified intrinsic vectors is determined. These values are the starting values for the main determination in the subsequent steps. The controller 106 the continues to step S8.

In step S8, the controller 106 begins the analysis of the full set of equations with possible perturbation of the intrinsic state vectors. The normal equations, including the perturbations, are the partial derivatives of the sum of squares equation with respect to each of the proportions individually. The derivatives of the proportion of each intrinsic state vector, and, separately, the proportions of each of the possible perturbations to any subset of the intrinsic state vectors are used. The controller 106 proceeds to step S9 as shown in FIG. 7B.

In step S9, the controller 106 stores two sets of derivative values, a current set and a previous set. The controller 106 continues to step S10.

In step S10, the controller 106 determines the sign of the current and previous sets of derivatives. When the controller 106 first enters step S10 from step S9, all signs are equal because the signs are initialized to be equal. The controller 106 continues to step S11.

In step S11, the controller 106 determines for each of the proportions whether the sign of the current and the previous derivatives has changed, i.e. from positive to negative or negative to positive. If the sign has changed, then the controller 106 continues to step S12; otherwise, the controller 106 jumps to step S13.

In step S12, the controller 106 reduces the percentage increment size for determining the estimated state vector set of percentages. This increment is initially set to a small number, usually of the order to $10^{-3}$, consistent with the accuracy of the best modern instrumentation. The reduction of the increment is by a small factor. An example would be multiplication by 0.99. After the increment is reduced in step S12, the controller 106 goes to step S13.

In step S13, the controller 106 increments each proportion in the appropriate direction. The direction is determined by whether the derivative is positive or negative. If positive, the controller 106 decrements the percentage value, and, if negative, the controller 106 increments the percentage value. The controller 106 continues to step S14. In step S14, the controller 106 stores the current and previous partial derivatives. The controller continues to step S15.

In step S15, the controller 106 determines the new sum of squares using the new incremented percentage values determined in step S13. The controller 106 continues to step S16. In step S16 the controller 106 determines new partial derivatives utilizing the new incremented percentage values in the normal equations. The controller 106 continues to step S17.

In step S17 the controller 106 tests whether the previous sum of squares minus the newly determined sum of squares, divided by the previous sum of squares, is less than the preset value. If the test result is yes, then the controller 106 continues to step S18 where the controller 106 outputs a best fit estimated state vector and stops. If the test result is no, then the controller 106 returns to step S10 and continues the estimation process.

An example of a program in POWER BASIC® performing the functions of the flow charts shown in FIGS. 7A and 7B is as follows:

- 20 -

In step S13, the controller 106 increments each proportion in the appropriate direction. The direction is determined by whether the derivative is positive or negative. If positive, the controller 106 decrements the percentage value, and, if negative, the controller 106 increments the percentage value. The controller 106 continues to step S14. In step S14, the controller 106 stores the current and previous partial derivatives. The controller continues to step S15.

In step S15, the controller 106 determines the new sum of squares using the new incremented percentage values determined in step S13. The controller 106 continues to step S16. In step S16 the controller 106 determines new partial derivatives utilizing the new incremented percentage values in the normal equations. The controller 106 continues to step S17.

In step S17 the controller 106 tests whether the previous sum of squares minus the newly determined sum of squares, divided by the previous sum of squares, is less than the preset value. If the test result is yes, then the controller 106 continues to step S18 where the controller 106 outputs a best fit estimated state vector and stops. If the test result is no, then the controller 106 returns to step S10 and continues the estimation process.

An example of a program in POWER BASIC$^\epsilon$ performing the functions of the flow charts shown in Figs. 7A and 7B is as follows:

```
'ULTRA-STREAMLINED ABSOLUTE PROCESS OF FITTING CD DATA
'BY MODIFIED INTRINSIC BASE STATES (mibs). CALCULATES FREE ENERGY
'AND MODIFIED DENATURED STATE VECTOR $FLOAT NPX
$CPU 80386
$OPTIMIZE SPEED
$ERROR ALL ON
DEFEXT A-Z
```

- 21 -

```
        CLS
        DIM RHS40##(100)
        DIM RHS95##(100)
        DIM RRHS95##(100)
5       DIM CDDATA##(100)
        DIM DECONDATA##(100)
        DIM ALPHADATA##(100)
        DIM BETADATA##(100)
        DIM RCDATA##(100)
10      DIM AROMDATA##(100)
        DIM BTURNDATA##(100)

INPUT "NAME OF DENATURED PROTEIN SOURCE FILE"DENFILE$
        INPUT "NAME OF NATIVE PROTEIN SOURCE FILE"NATEFILE$

INPUT "DO YOU WISH TO USE FASMAN DATA (ENTER F) OR
15      MODIFIED FASMAN WITH HIGH TEMPERATURE RC VECTOR (ENTER
        M)"DATABASECHOICE$
        IF (DATABASECHOICE$="F") OR (DATABASECHOICE$="f") THEN
        OPEN DENFILE$ FOR INPUT AS #1
        OPEN NATEFILE$ FOR INPUT AS #2
20      BASISFILE$="BASICRCS.DAT"
        OPEN BASISFILE$ FOR INPUT AS #3

ELSEIF (DATABASECHOICE$="M") OR (DATABASECHOICE$="m")
        THEN
        OPEN DENFILE$ FOR INPUT AS #1
25      OPEN NATEFILE$ FOR INPUT AS #2
        BASISFILE$="BASICRC2.CSV"
        OPEN BASISFILE$ FOR INPUT AS #3
        ELSE
        PRINT "YOU MUST CHOOSE ONE BASE STATE OR THE OTHER"
30      END
        END IF
        CLS
        FOR Z%=1 TO 46
```

- 22 -

```
           INPUT #1,WAVELENGTH,RHS95##(Z%)
           INPUT #2,WAVELENGTH,RHS40##(Z%)
        NEXT Z%
        CLOSE #1
 5      CLOSE #2
        INPUT "DO YOU WISH TO NORMALIZE THE NATIVE VECTOR, Y OR
        N"NVECTORCHOICE$
        INPUT "DO YOU WISH TO NORMALIZE THE DENATURED STATE
        VECTOR, Y OR N"DVECTORCHOICE$

10      IF (DVECTORCHOICE$="Y") OR (DVECTORCHOICE$="y") THEN
        INPUT "PERCENT NATIVE STATE BELIEVED PRESENT IN DENATURED
        STATE VECTOR"PNAT##
        PNAT##=.01*PNAT##
        FOR Z%=1 TO 46    'RENORMALIZE 95 C DATA
15      RHS95##(Z%)=RHS95##(Z%)-PNAT##*RHS40##(Z%)
        RHS95##(Z%)=RHS95##(Z%)/(1-PNAT##)
        NEXT Z%
        END IF

IF (NVECTORCHOICE$="Y") OR (NVECTORCHOICE$="y") THEN
20      INPUT "PERCENT DENATURED STATE BELIEVED PRESENT IN NATIVE
        STATE VECTOR"PDEN##
        PDEN##=.01*PDEN##
        FOR Z%=1 TO 46   'RENORMALIZE NATIVE STATE DATA
        DECONDATA##(Z%)=RHS40##(Z%)
25      DECONDATA##(Z%)=DECONDATA##(Z%)-PDEN##*RHS95##(Z%)
        DECONDATA##(Z%)=DECONDATA##(Z%)/(1-PDEN##)
        RHS40##(Z%)=DECONDATA##(Z%)
        NEXT Z%
        END IF

30      FOR Z%=1 TO 46
          INPUT
        #3,AAA,ALPHADATA##(Z%),BTURNDATA##(Z%),AROMDATA##(Z%),RCD
        ATA##(Z%),BETADATA##(Z%)
```

- 23 -

```
        NEXT Z%
        CLOSE #3

INPUT "NAME OF FILE TO BE DECONVOLUTED"INPUTFILE$
          INPUT "NAME OF FILE TO STORE THE DECONVOLUTED
 5      DATA"STOREFILE$
          CLS
          FILENO=FREEFILE
          OPEN INPUTFILE$ FOR INPUT AS #FILENO

MEAN##=0
10      FOR Z%=1 TO 46
          INPUT #FILENO,WAVELENGTH#,CDDATA##(Z%)
          MEAN##=MEAN##+CDDATA##(Z%)
        NEXT Z%
        MEAN##=MEAN##/46
15      MEANSQ##=0

FOR Z%=1 TO 46
        MEANSQ##=MEANSQ##+(MEAN##-CDDATA##(Z%))^2
        NEXT Z%

CLOSE #FILENO

20      CLS
                        'CALCULATE IBS SUM OF SQUARES, THAT IS,
        ALL PERTURBATION VECTORS=0
                        PREVSUMOFSQUARES##=SUMOFSQUARES##
                            SUMOFSQUARES##=0
25                          NUMSUM##=0
                            DENSUM##=0
                        FOR WAVE%=1 TO 46

NUMSUM##=NUMSUM##+RHS95##(WAVE%)-CDDATA##(WAVE%)
```

- 24 -

```
        DENSUM##=DENSUM##+RHS95##(WAVE%)-RHS40##(WAVE%)
                        NEXT WAVE%
                        NATIVE##=NUMSUM##/DENSUM##
5                       DENATURED##=1-NATIVE##

FOR WAVE%=1 TO 46

SUM##=NATIVE##*RHS40##(WAVE%)+DENATURED##*RHS95##(WAVE%)

10      DIFFERENCE##=SUM##-CDDATA##(WAVE%)

DIFFERENCE##=DIFFERENCE##*DIFFERENCE##

SUMOFSQUARES##=SUMOFSQUARES##+DIFFERENCE##
15                      NEXT WAVE%
                        STSUMOFSQUARES##=SUMOFSQUARES##
                        'SUMOFSQUARES##=0
                        PRINT "NATIVE= "NATIVE##
                        SLEEP

20                      PARTIALBYA##=0
                        PARTIALBYB2##=0
                        PARTIALBYB3##=0
                        PARTIALBYB4##=0
                        PARTIALBYB5##=0

25                      FOR Z%=1 TO 46

PARTIALBYA##=PARTIALBYA##+(CDDATA##(Z%)-NATIVE##*RHS40##(
        Z%)+DENATURED##*RHS95##(Z%))*(-RHS40##(Z%)+RHS95##(Z%))

30      PARTIALBYB2##=PARTIALBYB2##+(CDDATA##(Z%)-NATIVE##*RHS40#
        #(Z%)+DENATURED##*RHS95##(Z%))*(-DENATURED##*(BTURNDATA##
        (Z%)-ALPHADATA##(Z%)))
```

- 25 -

```
        PARTIALBYB3##=PARTIALBYB3##+(CDDATA##(Z%)-NATIVE##*RHS40#
        #(Z%)+DENATURED##*RHS95##(Z%))*(-DENATURED##*(AROMDATA##(
        Z%)-ALPHADATA##(Z%)))
5
        PARTIALBYB4##=PARTIALBYB4##+(CDDATA##(Z%)-NATIVE##*RHS40#
        #(Z%)+DENATURED##*RHS95##(Z%))*(-DENATURED##*(RCDATA##(Z%
        )-ALPHADATA##(Z%)))

10      PARTIALBYB5##=PARTIALBYB5##+(CDDATA##(Z%)-NATIVE##*RHS40#
        #(Z%)+DENATURED##*RHS95##(Z%))*(-DENATURED##*(BETADATA##(
        Z%)-ALPHADATA##(Z%)))
                    NEXT Z%
                    PREVPARTIALBYA##=PARTIALBYA##
15                  PREVPARTIALBYB2##=PARTIALBYB2##
                    PREVPARTIALBYB3##=PARTIALBYB3##
                    PREVPARTIALBYB4##=PARTIALBYB4##
                    PREVPARTIALBYB5##=PARTIALBYB5##

A##=NATIVE##    'START WITH OPTIMAL IBS
20      PROPORTIONS
                    INCR1##=.001
                    INCR2##=.001
                    INCR3##=.001
                    INCR4##=.001
25                  INCR5##=.001
                    TESTDIF##=1
                    DO WHILE TESTDIF##>.0000001

SIGNA##=SGN(PARTIALBYA##)
                    SIGNB2##=SGN(PARTIALBYB2##)
30                  SIGNB3##=SGN(PARTIALBYB3##)
                    SIGNB4##=SGN(PARTIALBYB4##)
                    SIGNB5##=SGN(PARTIALBYB5##)

SIGNPA##=SGN(PREVPARTIALBYA##)
```

- 26 -

```
SIGNPB2##=SGN(PREVPARTIALBYB2##)
SIGNPB3##=SGN(PREVPARTIALBYB3##)
SIGNPB4##=SGN(PREVPARTIALBYB4##)
SIGNPB5##=SGN(PREVPARTIALBYB5##)

IF SIGNA##=SIGNPA## THEN
 IF SIGNA##<0 THEN
        INCR A##, INCR1##
         'BIT RESET STATICCOUNT?,0
       ELSEIF SIGNA##>0 THEN
         INCR A##,-INCR1##
         'BIT RESET STATICCOUNT?,0
       END IF
      ELSE
       IF SIGNA##<0 THEN
         INCR1##=INCR1##*0.99
         INCR A##, INCR1##
         'BIT RESET STATICCOUNT?,0
       ELSEIF SIGNA##>0 THEN
         INCR1##=INCR1##*0.99
         INCR A##,-INCR1##
         'BIT RESET STATICCOUNT?,0
       END IF

'BIT SET STATICCOUNT?,0
      END IF

IF SIGNB2##=SIGNPB2## THEN
       IF SIGNB2##<0 THEN
         INCR B2##, INCR2##
         'BIT RESET STATICCOUNT?,1
       ELSEIF SIGNA##>0 THEN
         INCR B2##,-INCR2##
         'BIT RESET STATICCOUNT?,1
       END IF
      ELSE
       IF SIGNB2##<0 THEN
         INCR2##=INCR2##*0.99
```

```
                            - 27 -
                    INCR B2##, INCR2##
                     'BIT RESET STATICCOUNT?,1
                  ELSEIF SIGNA##>0 THEN
                    INCR2##=INCR2##*0.99
                    INCR B2##,-INCR2##
                     'BIT RESET STATICCOUNT?,1
                  END IF
                  'BIT SET STATICCOUNT?,1
                END IF

IF SIGNB3##=SIGNPB3## THEN
          IF SIGNB3##<0 THEN
                  INCR B3##, INCR3##
                   'BIT RESET STATICCOUNT?,2
                ELSEIF SIGNA##>0 THEN
                  INCR B3##,-INCR3##
                   'BIT RESET STATICCOUNT?,2
                END IF
              ELSE
              IF SIGNB3##<0 THEN
                 INCR3##=INCR3##*0.99
                 INCR B3##, INCR3##
                  'BIT RESET STATICCOUNT?,2
                ELSEIF SIGNA##>0 THEN
                  INCR3##=INCR3##*0.99
                  INCR B3##,-INCR3##
                   'BIT RESET STATICCOUNT?,2
                END IF
                'BIT SET STATICCOUNT?,2
              END IF

IF SIGNB4##=SIGNPB4## THEN
              IF SIGNB4##<0 THEN
                INCR B4##, INCR4##
                 'BIT RESET STATICCOUNT?,3
              ELSEIF SIGNB4##>0 THEN
                INCR B4##,-INCR4##
```

```
                      - 28 -
                    'BIT RESET STATICCOUNT?,3
                   END IF
                 ELSE
                 IF SIGNB4##<0 THEN
                    INCR4##=INCR4##*0.99
                    INCR B4##, INCR4##
                    'BIT RESET STATICCOUNT?,3
                   ELSEIF SIGNB4##>0 THEN
                    INCR4##=INCR4##*0.99
                    INCR B4##,-INCR4##
                    'BIT RESET STATICCOUNT?,3
                   END IF
                   'BIT SET STATICCOUNT?,3
                 END IF

IF SIGNB5##=SIGNPB5## THEN
        IF SIGNB5##<0 THEN
                  INCR B5##, INCR5##
                   'BIT RESET STATICCOUNT?,4
                  ELSEIF SIGNA##>0 THEN
                   INCR B5##,-INCR5##
                   'BIT RESET STATICCOUNT?,4
                  END IF
                 ELSE
                 IF SIGNB5##<0 THEN
                    INCR5##=INCR5##*0.99
                    INCR B5##, INCR5##
                    'BIT RESET STATICCOUNT?,4
                   ELSEIF SIGNA##>0 THEN
                    INCR5##=INCR5##*0.99
                    INCR B5##,-INCR5##
                    'BIT RESET STATICCOUNT?,4
                   END IF
                   'BIT SET STATICCOUNT?,4
                 END IF
```

- 29 -

```
        PREVPARTIALBYA##=PARTIALBYA##
        PREVPARTIALBYB2##=PARTIALBYB2##
        PREVPARTIALBYB3##=PARTIALBYB3##
        PREVPARTIALBYB4##=PARTIALBYB4##
5       PREVPARTIALBYB5##=PARTIALBYB5##

PARTIALBYA##=0
        PARTIALBYB2##=0
        PARTIALBYB3##=0
        PARTIALBYB4##=0
10      PARTIALBYB5##=0

PREVSUMOFSQUARES##=SUMOFSQUARES##
        SUMOFSQUARES##=0   :  AN1##=A##-1
        FOR Z%=1 TO 46   'RAW SUM OF SQUARES

15      PERTURB##=(RHS95##(Z%)-(B2##+B3##+B4##+B5##)*ALPHADATA##(
        Z%)+B2##*BTURNDATA##(Z%)+B3##*AROMDATA##(Z%)+B4##*RCDATA#
        #(Z%)+B5##*BETADATA##(Z%))

KERNEL##=(CDDATA##(Z%)-A##*RHS40##(Z%)+(A##-1)*(RHS95##(Z
20      %)-(B2##+B3##+B4##+B5##)*ALPHADATA##(Z%)+B2##*BTURNDATA##
        (Z%)+B3##*AROMDATA##(Z%)+B4##*RCDATA##(Z%)+B5##*BETADATA#
        #(Z%)))
                    SUMOFSQUARES##=SUMOFSQUARES##+KERNEL##^2

25      PARTIALBYA##=PARTIALBYA##+KERNEL##*(-RHS40##(Z%)+PERTURB#
        #)

PARTIALBYB2##=PARTIALBYB2##+KERNEL##*AN1##*(BTURNDATA##(Z
        %)-ALPHADATA##(Z%))
30
        PARTIALBYB3##=PARTIALBYB3##+KERNEL##*AN1##*(AROMDATA##(Z%
        )-ALPHADATA##(Z%))
```

- 30 -

```
    PARTIALBYB4##=PARTIALBYB4##+KERNEL##*AN1##*(RCDATA##(Z%)-
    ALPHADATA##(Z%))

5   PARTIALBYB5##=PARTIALBYB5##+KERNEL##*AN1##*(BETADATA##(Z%
    )-ALPHADATA##(Z%))
              NEXT Z%

TESTDIF##=ABS((PREVSUMOFSQUARES##-SUMOFSQUARES##)/PREVSUM
10  OFSQUARES##)
              LOCATE 12,13
              PRINT "TOTAL SUM OF SQUARES ="MEANSQ##
              PRINT "IBS SUM OF SQUARES= "STSUMOFSQUARES##
              PRINT "SUM OF SQUARES = "SUMOFSQUARES##
15            PRINT "NATIVE %="100*A##
              PRINT "DENATURED %= "100*(1-A##)
              PRINT "ALPHA % ="-100*(B2##+B3##+B4##+B5##)
              PRINT "BETA TURN % ="100*B2##
              PRINT "AROMATICS % ="100*B3##
20            PRINT "RC % ="100*B4##
              PRINT "BETA SHEET % ="100*B5##
           LOOP

BEEP : BEEP : BEEP
    PRINT "HIT ANY KEY TO CONTINUE"
25  SLEEP
    CLS

OPEN STOREFILE$ FOR OUTPUT AS #1
       WRITE #1,"DATA FROM MODIFIED INTRINSIC PROGRAM DECNVL8S
       WRITE #1,"DENATURED STATE SOURCE FILE",DENFILE$
30     WRITE #1,"NATIVE STATE SOURCE FILE",NATEFILE$
       WRITE #1,"TEST DATA SOURCE FILE",INPUTFILE$
       WRITE #1,"BASIS STATES SOURCE FILE",BASISFILE$
```

- 31 -

```
        IF (NVECTORCHOICE$="Y")  OR (NVECTORCHOICE$="y") THEN
             WRITE #1,"NATIVE STATE NORMALIZED,PERCENT
        DENATURED STATE BELIEVED PRESENT IN NATIVE STATE
        VECTOR",100*PDEN##
5       END IF
        IF (DVECTORCHOICE$="Y")  OR (DVECTORCHOICE$="y") THEN
             WRITE #1,"DENATURED STATE NORMALIZED,PERCENT
        NATIVE STATE BELIEVED PRESENT IN DENATURED STATE
        VECTOR",100*PNAT##
10      END IF
        WRITE #1, "TOTAL SUM OF SQUARES=",MEANSQ##
        WRITE #1, "MINIMUM SUM OF SQUARES=",SUMOFSQUARES##
        WRITE #1, "BEST % 95=",100*(1-A##)
        WRITE #1, "BEST % NATIVE STATE=",100*A##
15      WRITE #1,  "BEST % ALPHA=
        ",ROUND(-100*(B2##+B3##+B4##+B5##),2)
        WRITE #1,  "BEST % BETA TURN= ",ROUND(100*B2##,2)
        WRITE #1,  "BEST % AROMATICS= ",ROUND(100*B3##,2)
        WRITE #1,  "BEST % RANDOM COIL= ",ROUND(100*B4##,2)
20      WRITE #1,  "BEST % BETA SHEET= ",ROUND(100*B5##,2)

SCREEN 12
        WINDOW (190,-25)-(245,25)
        LINE (190,0)-(245,0)
        LINE (190,-25.00)-(190,25.00)

25      FOR M= 1 TO 46
        LINE (190+M,-1)-(190+M,1)
        LINE (190,-M)-(190+1,-M)
        LINE (190,M)-(190+1,M)
        NEXT M
30      PRINT "GREEN IS 95 C VECTOR AT TEST TEMP MODIFIED BY
        PERTURBATION VECTORS"
        PRINT "RED IS DENATURED VECTOR AT TEST TEMP CALCULATED "
        PRINT  "BY SUBTRACTION OF NATIVE VECTOR FROM RAW DATA,
        THEN RENORMALIZATION"
```

- 32 -

```
       FOR Z%=1 TO 46

RRHS95##(Z%)=RHS95##(Z%)-(B2##+B3##+B4##+B5##)*ALPHADATA#
       #(Z%)+B2##*BTURNDATA##(Z%)+B3##*AROMDATA##(Z%)+B4##*RCDAT
       A##(Z%)+B5##*BETADATA##(Z%)
5      WAVE%=194+Z%
       DECONDATA##(Z%)=CDDATA##(Z%)-(RHS40##(Z%)*A##)
       DECONDATA##(Z%)=DECONDATA##(Z%)/(1-A##)
       CIRCLE (WAVE%,RRHS95##(Z%)),.25,2
       PAINT (WAVE%,RRHS95##(Z%)),2
10     CIRCLE (WAVE%,DECONDATA##(Z%)),.25,4
       'RED,DENATURED AT TEST
       PAINT (WAVE%,DECONDATA##(Z%)),4
       NEXT Z%

BEEP
15     SLEEP
       CLS
       WINDOW (190,-25)-(245,25)
       LINE (190,0)-(245,0)
       LINE (190,-25.00)-(190,25.00)

20     FOR M= 1 TO 46
       LINE (190+M,-1)-(190+M,1)
       LINE (190,-M)-(190+1,-M)
       LINE (190,M)-(190+1,M)
       NEXT M
25     PRINT "BLUE IS TEST DATA"
       PRINT "PURPLE IS THE FIT"
       FOR Z%=1 TO 46
       WAVE%=194+Z%
       DECONDATA##(Z%)=(RRHS95##(Z%)*(1-A##)+RHS40##(Z%)*A##)
30     WRITE
       #1,WAVE%,ROUND(RRHS95##(Z%),4),ROUND(CDDATA##(Z%),4),ROUN
       D(DECONDATA##(Z%),4)
         CIRCLE (WAVE%,CDDATA##(Z%)),.1,3
         PAINT (WAVE%,CDDATA##(Z%)),3
35       CIRCLE (WAVE%,DECONDATA##(Z%)),.1,5
```

- 33 -

```
PAINT (WAVE%,DECONDATA##(Z%)),5
NEXT Z%
CLOSE
SLEEP
END
```

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A method for determining a proportion of a plurality of intrinsic structures of an optically active substance within a sample of the optically active substance, the method comprising:

generating a plurality of intrinsic spectra, each intrinsic spectrum corresponding to one of the plurality of intrinsic structures of the optically active substance;

generating a plurality of estimated spectra, each estimated spectrum corresponding to a proportional combination of at least two perturbed intrinsic structures of the optically active substance;

generating a sample spectrum from the sample of the optically active substance;

selecting a best match estimated spectrum from the plurality of estimated spectra which most closely match the sample spectrum of the optically active substance; and outputting the proportional combination of the best match estimated spectrum as the proportional combination of the plurality of perturbed intrinsic structures in the sample of the optically active substance.

2. The method of claim 1, wherein generating a plurality of intrinsic spectra comprises:

defining a plurality of intrinsic samples, each of the plurality of intrinsic samples corresponding to one of the plurality of intrinsic structures of the optically active substance;

generating a plurality of polarized light beams, each beam corresponding to one of a plurality of wavelengths; and illuminating each of the plurality of intrinsic samples with the plurality of polarized light beams to obtain one of the plurality of intrinsic spectra.

3. The method of claim 2, wherein the generating the sample spectrum comprises illuminating the sample of the optically active substance with the plurality of polarized light beams to generate the sample spectrum of the optically active substance.

4. The method of claim 3, wherein each of the plurality of intrinsic structures of the optically active substance comprises a plurality of pure molecular forms, wherein the determining the plurality of estimated spectra comprises:

generating a plurality of pure molecular form spectra corresponding to the plurality of wavelengths of the polarized light beams;

generating a plurality of perturbed intrinsic spectra corresponding to each intrinsic spectrum, each perturbed intrinsic spectrum generated by perturbing a corresponding intrinsic spectra using one of the pure molecular form spectrum;

generating a plurality of sets of estimated perturbed intrinsic spectra, each set of perturbed intrinsic spectra comprising one of the plurality of perturbed intrinsic spectra corresponding to each of the plurality of intrinsic spectra;

determining an optimal proportional combination for each set of the estimated perturbed intrinsic spectra; and generating the plurality of estimated spectra based on the optimum proportional combination for each set of estimated perturbed intrinsic spectra.

5. The method of claim 4, wherein generating one of the plurality of perturbed intrinsic spectra comprises adding and subtracting percentages of each of the plurality of pure molecular form spectra to/from each of the plurality of intrinsic spectra, the sum of all the percentages of adds and subtracts being equal to zero.

6. The method of claim 4, wherein each of the plurality of estimated spectra is generated by summing the corresponding optimum proportional combination of one set of the plurality of estimate perturbed intrinsic spectra.

7. The method of claim 1, wherein selecting one of the plurality of estimated spectra comprises:

determining a plurality of differences, each of the plurality of differences being a difference between each of the plurality of estimated spectra and the sample spectra of the optically active substance;

determining a plurality of sum of squares of the difference, each of the plurality of sum of squares of the difference corresponding to each of the plurality of estimated spectra; and selecting one of the plurality of estimated spectra corresponding to one of the plurality of sum of squares of the difference having the lowest value as the best match to the sample spectra of the optically active substance.

8. The method of claim 4, wherein the plurality of pure molecular forms comprises at least an alpha-helix, a beta-sheet and a random coil.

9. A device for determining a proportional combination of a plurality of intrinsic structures of an optically active substance in a sample of the optically active substance, comprising:

a spectrum generating device;

an I/O device inputting spectrum data generated by the spectrum generating device;

a memory device coupled to the I/O device storing spectrum data corresponding to intrinsic spectra and a sample spectrum of the optically active substance;

estimated spectra determining means for determining a plurality of estimate spectra based on the plurality of intrinsic spectra; and best match selection means for selecting one of the plurality of estimated spectra as a best match estimated spectra which most closely matches the sample spectra of the optically active substance; and a controller controlling the I/O device, the memory device, the estimated spectra determining means and the best match selection means to determine the proportional combination of the plurality of intrinsic structures of the sample of the optically active substance.

10. The device of claim 9, wherein each estimated spectrum is a sum of a proportional combination of a set of perturbed intrinsic spectra, each of the set of perturbed intrinsic spectra corresponding to a perturbed intrinsic structure of the optically active substance, each estimated spectra corresponding to a proportional combination of the perturbed intrinsic structures of the optically active substance.

11. The device of claim 9, wherein the estimated spectra determining means comprises:

intrinsic spectra perturbing means for generating a plurality of perturbed intrinsic spectra;

estimated perturbed intrinsic spectra determining means for generating a plurality of sets of estimated perturbed intrinsic state vectors, each set of perturbed intrinsic spectra comprising one of the plurality of perturbed intrinsic spectra corresponding to each of the plurality of intrinsic spectra;

optimal proportional combination determining means for determining an optimal proportional combination for each set of the estimated perturbed intrinsic spectra;

estimated spectra generating means for generating the plurality of estimated spectra based on the optimum proportional combination for each set of estimated perturbed intrinsic spectra.

12. The device of claim 11, wherein intrinsic spectra perturbing means comprises means for adding and subtracting percentages of each of a plurality of pure molecular form spectra to/from each of the plurality of intrinsic spectra, the sum of all the percentages of adds and subtracts being equal to zero.

13. The device of claim 11, wherein the estimated spectra generating means generates each estimated spectrum by summing the corresponding optimum proportional combination of one set of the plurality of estimate perturbed intrinsic spectra.

14. The device of claim 9, wherein the spectrum generating device is a spectropolarimeter.

15. The device of claim 9, wherein the I/O device, the memory device, the estimated spectra determining means, the best match selection means and the controller is a general purpose computer.

* * * * *